United States Patent [19]

Hall et al.

[11] 4,268,424

[45] May 19, 1981

[54] DETERGENT BARS CONTAINING DI-, HYDROXY AND/OR AMINO-CARBOXYLIC ACID MOISTURIZERS

[75] Inventors: Norman Hall, Wirral; Alexander Martin, Warrington; Alan D. Tomlinson, Neston, all of England

[73] Assignee: Lever Brothers Company, New York, N.Y.

[21] Appl. No.: 89,681

[22] Filed: Oct. 30, 1979

Related U.S. Application Data

[63] Continuation of Ser. No. 953,338, Oct. 20, 1978, abandoned, which is a continuation of Ser. No. 858,123, Dec. 6, 1977, abandoned, which is a continuation of Ser. No. 731,171, Oct. 12, 1976, abandoned, which is a continuation of Ser. No. 432,120, Jan. 9, 1974, abandoned.

[30] Foreign Application Priority Data

Jan. 15, 1973 [GB] United Kingdom ............... 1994/73
Jul. 25, 1973 [GB] United Kingdom ............... 35528/73

[51] Int. Cl.$^3$ .................. C11D 3/33; C11D 3/20; C11D 17/00
[52] U.S. Cl. .................. 252/546; 252/89.1; 252/174; 252/174.19; 252/DIG. 5; 252/DIG. 16
[58] Field of Search ............. 252/DIG. 5, DIG. 16, 252/546, 142, 117, 174, 134, 132, 89.1, 174.19

[56] References Cited

U.S. PATENT DOCUMENTS

| | | | |
|---|---|---|---|
| 2,792,348 | 5/1957 | Aylesworth | 252/132 |
| 2,894,912 | 7/1959 | Geitz | 252/117 |
| 3,043,779 | 7/1962 | Parke et al. | 252/132 X |
| 3,085,066 | 4/1963 | Mituray | 252/107 |
| 3,376,229 | 4/1968 | Haass et al. | 252/117 |
| 3,442,812 | 5/1969 | Barnhurst et al. | 252/142 |
| 3,557,006 | 1/1971 | Ferrara et al. | 252/132 |
| 3,879,309 | 4/1975 | Gatti et al. | 252/117 |
| 4,046,717 | 9/1977 | Johnston et al. | 252/DIG. 16 X |

*Primary Examiner*—Harris A. Pitlick
*Attorney, Agent, or Firm*—James J. Farrell; Melvin H. Kurtz

[57] ABSTRACT

Detergent bars and liquids/pastes for topical application are given moisturizing properties by the use of materials selected from dicarboxylic acids and their salts, hydroxy acids and their salts and amino acids and their salts. Examples are adipic acid, maleic acid and glycine; in the bars these moisturizing components are usually present at a level of above 20%.

4 Claims, No Drawings

DETERGENT BARS CONTAINING DI-, HYDROXY AND/OR AMINO-CARBOXYLIC ACID MOISTURIZERS

This application is a continuation of application Ser. No. 953,338 filed on Oct. 20, 1978 and now abandoned which was a continuation of application Ser. No. 858,123 filed Dec. 6, 1977 and now abandoned which was a continuation of Ser. No. 731,171 filed on Oct. 12, 1976 and now abandoned which was a continuation of Ser. No. 432,120 filed on Jan. 9, 1974 and now abandoned.

This invention relates to detergent bars for use in personal washing. The bars will contain materials selected from soaps, i.e. alkali metal salts of long-chain fatty acids and synthetic detergent actives.

It is known to increase the water retention of skin by incorporating in a lotion, intended for topical application, a moisturising component. This component increases the water holding capacity of the skin.

The applicants have found that compounds within specific chemical classes increase the water retention properties of skin. These compounds are usable in detergent bars and lotions intended for topical application. The classes of compounds to which this application relates are:

(i) Dicarboxylic acids with the formula:

$$COOH-(CH_2)_n-COOH$$

and their water soluble salts n is from 2 to 8, preferably 2 to 6 and the hydrocarbon chain may be branched. The hydrocarbon chain may be saturated or unsaturated.

(ii) Hydroxy acids with the formula:

$$R_1R_2.C(OH)COOH$$

where $R_1$ and $R_2$ are each hydrogen or a short chain ($C_1$ to $C_4$) alkyl group, which may be branched and/or unsaturated, or $-CH_2COOH$, or $-CH(OH)COOH$;

(iii) Amino-acids with the formula:

$$R_1R_2C(NH_2)COOH$$

where $R_1$ and $R_2$ are each hydrogen or a short chain ($C_1$ to $C_4$) alkyl, hydroxyalkyl, preferably monohydroxyalkyl, carboxyalkyl group, or amino-alkyl group which may be branched and/or unsaturated (the carbon chain refers to the alkyl groups), and the water soluble salts of these classes of acids. Preferably the carboxy alkyl group is $COOH-CH_2-$ (i.e. $R_1$ or $R_2$ is $C_2$).

Preferred members of class (ii) are tartaric acid, citric acid, acetonic acid, glycollic acid and molic acid.

Preferred members of class (i) are succinic acid, glutaric acid, adipic acid, azelaic acid, sebacic acid, fumaric acid and itaconic acid.

Examples of class (iii) are glycine, alanine, valine, leucine, isoleucine, threonine and serine. Aspartic acid is also included.

The applicants propose the use of acids of these classes and their water soluble salts in lotions and detergent bars at a level sufficient to increase the water retention capacity of the skin. The level of use in a bar will usually be above about 5%, preferably above about 10% and more preferably above about 20% by weight. These compounds may be used as mixtures to a total amount as proposed above, thus 2.5% of each of two compounds proposed could be used. The upper limit of inclusion of these materials is set by the processing and in-use characteristics of the product. For bars the upper limit will be about 55% of the moisturising component. The water soluble salts will normally be alkali metal salts for example sodium, potassium or alkanolamine or ammonium salts. The bars will contain from about 45% to about 80% by weight of detergent active material and additives known for use in a detergent bar.

The applicants have found that one or more of these components can be incorporated in detergent bars having usable physical properties. That is to say the properties, for example, mushing, extrudability and wear are sufficient for an acceptable bar. Further the applicants have found that these moisturising components act on the skin in a rinse-off situation, i.e. one in which a washing bar is used to wash the skin and wash liquor rinsed off relatively soon after the washing stage.

Any moisturizer used may contain free acid dependant on the pH of the detergent active material. The term water soluble salt used herein includes any free acid which may be present. Amino-acids may be present as the cationic form, for example as the hydrochloride.

Examples of detergent actives used to form the detergent bar of the invention are in the following classes (other actives are disclosed in "Surface Active Agents" by Schwartz & Perry published by Interscience in 1949 and volume II by Schwartz, Perry & Berch published by Interscience (1958):

(a) isethionates containing an alkyl group having from 8 to 18 carbon atoms, such actives are termed "Igepon A" and may be derived from, for example, coconut fatty acids;

(b) alkali metal salts of alkane sulphonates having an alkyl chain length of from 11 to 14, these actives are prepared by the reaction of a bisulphite ion species with an olefin;

(c) sulphates of branched chain alcohols having chain lengths from 12 to 15, these alcohols are obtainable under the trade name "Dobanol;"

(d) alkylaryl sulphonates having an alkyl chain from $C_{10}$ to $C_{15}$;

(e) dialkali metal salts of sulphonated saturated fatty acids having a chain length from $C_{12}$ to $C_{20}$;

(f) ethoxylated alcohols ($C_{12}$ to $C_{20}$) having a degree of ethoxylation between 10 and 20;

(g) alkyl ($C_{12}$ to $C_{18}$) sulphates, having a degree of branching at the alpha position of up to 25%;

(h) alkene sulphonates having a chain length from $C_{14}$ to $C_{24}$;

(i) alkali metal salts of $C_8$ to $C_{22}$ long chain fatty acids; and (j) nonionic detergent actives, for example polyoxyalkylene derivatives of alcohols, alkyl amides and alkanolamides, polyoxyalkylene esters of acids, alkylene oxide block polymers (e.g. PLURONICS), polyol esters and acyl alkanolamides.

Other examples of actives are amphoterics, betaine and cationics, e.g. ethoxylated quaternaries.

The bars may contain other materials, for example water, usually present in an amount up to 20%, pH controllers, germicides, perfumes and plasticisers.

The detergent bars of the invention may also contain other components which moisturize the skin during washing for example 2-pyrrolidone-5-carboxylic acid and its salts, hydrolised proteins, salts of N-acetyl glycine.

Mixtures of the detergent actives can be used, for example
(i) a mixture of alkane sulphonates and alkene sulphonates as disclosed in UK Pat. No. 1,171,616, and
(ii) a mixture of tallow alcohol 16 EO and Igepon A.

The moisturizing component can be added at any stage in the processing of the bar provided the component is not subjected to processing steps leading to its degradation.

The components may be added as the free acid or salt dependant on the pH of detergent active used, i.e. with a very alkaline active material the free acid may be added so that the salt is formed in the bar. A moisturising effect is obtained from free acid present in a detergent bar by the formation of the corresponding salt when the free acid contacts the skin. The components may exist in the dextro-or laevo-form, but the present invention does not depend on the isomer used.

Examples of detergent bars of the invention will now be given.

The water retention tests were performed using a method similar to that described by A C Park and C B Daddiel in the Journal of the Society of Cosmetic Chemists, Volume 20 (1972) pages 13 to 21. In the measurements below the elastic modulus of guinea pig corneum is measured after soaking corneum in 10% solutions of the bars for periods up to 30 minutes followed by a rinse in distilled water for up to 5 minutes. The corneum was patted dry and suspended in an atmosphere at 90% relative humidity for 6 days to equilibrate. The elastic modulus (dynes per square centimeter) was then measured, a reduction in modulus shows increase in water retention. The results are quoted as log (modulus$\times 10^{-5}$) and reduction in the parameter demonstrates increased elasticity.

EXAMPLE I

The sodium salts were used.
Sodium tallow soap—3.73
Soap+5% malate+5% serine—3.59
Soap+5% succinate+5% glycine—3.54
Difference required for 95% confidence—0.13

EXAMPLE II

Bars made according to the invention used mixture A which contained:
Sodium coconut isethionate—78%
$C_{10}$-$C_{18}$ fatty acids—22%

Bars containing 5%, 10%, 20%, and 40% of compounds specified in a detergent base were found to increase the water binding capacity of corneum by measurement of elastic modulus and give a moisturising effect in handwashing tests. The detergent base contained mixture A and soap (58% tallow, 42% coconut) in a ratio of 1:1.

The compounds specified were:
malic acid
disodium malate
citric acid
sodium citrate
glycollic acid
sodium glycollate
tartaric acid
sodium tartarate
sodium 2-hydroxybutyrate
succinic acid
sodium glutarate
sodium adipate
itaconic acid
fumaric acid

EXAMPLE III

Moisturising components were also tested by measuring the increase in water binding capacity of epidermis from the back footpads of guinea pigs by contact with the components in a detergent system.

The test used damaged guinea pig corneum and the test method was as follows.

The rear footpads of guinea pigs are removed with a scalpel and incubated in buffered trypsin solution (pH 7.2) at 40° C. overnight. The remaining corneum is washed in distilled water for 4 hours. Damage (reduction in water binding capacity) is effected by soaking the corneum in ether overnight followed by washing in distilled water for 6 hours. The corneum is then ready for use.

Pieces of corneum are soaked in 10% solutions of surfactant+moisturizer(s) for periods up to 30 minutes followed by a rinse in distilled water for up to 5 minutes. The corneum is patted dry and suspended in an atmosphere at 90% relative humidity for 6 days to equilibrate. The corneum is weighed and re-equilibrated for a further 6 days in a dry atmosphere before reweighing.

The water binding capacity is calculated and expressed as the amount of water held by 100 mg dry corneum.

Test bars containing mixtures of the detergent active and the moisturising component were made up by mixing the materials at the primary stage. All the bars prepared had acceptable physical properties. The results are quoted as the amount of water (in mg) bound by 100 mg of the dry corneum.

|  | wbc |
| --- | --- |
| Igepon A (control) | 24.9 |
| sodium glycollate | 33.1 |
| sodium succinate | 33.6 |
| sodium tartarate | 33.5 |
| sodium citrate | 28.8 |
| lysine hydrochloride | 31.2 |
| Igepon A (control) | 31.9 |
| sodium sebacate | 34.4 |
| sodium azelate | 34.2 |
| sodium itaconate | 41.7 |
| sodium acetonate | 41.0 |

EXAMPLE IV

Example III was repeated using the detergent bases quoted below and moisturising agents. Detergent bases are quoted by reference letters A to F for convenience.
  A—80 parts tallow soap/20 parts coconut soap
  B—70 parts (35 tallow soap/09 (1:1) coconut soap/10 coconut fatty acid)
    30 parts sodium/potassium (1:1) Dobanol 25 sulphate
    0.5 parts white oil
    0.5 parts petroleum jelly
  C—78 parts sodium coconut isethionate
    22 parts $C_{10-18}$ fatty acid
  D—54 parts sodium coconut isethionate
    9 parts sodium tallow soap
    25 parts stearic acid
    7 parts sodium isethionate
    3 parts sodium dodecylbenzene sulphonate
  E—Tallow alcohol 18 EO F—30 parts $C_{11-14}$ alkane sulphonate
30 parts $C_{15-18}$ alkane sulphonate
40 parts $C_{14-18}$ olefin sulphonate Two series of experiments were performed each with their own controls, amounts are in weight percent.

| Detergent base | Moisturizer (sodium salts) | Water binding capacity |
|---|---|---|
| | First series | |
| 30% C, 30% A | 40% glycollate | 33.8 |
| 70% B | 30% alanine | 33.8 |
| 70% F | 30% fumarate | 33.4 |
| 35% C, 35% A | 30% malate | 33.4 |
| 40% C, 40% A | 10% glycollate, 10% itaconate | 32.8 |
| 18% C, 52% A | 20% adipate, 10% citrate | 31.4 |
| 40% C, 40% A | 15% glutamate, 5% tartarate | 31.4 |
| 35% C, 35% A | 30% tartarate | 30.8 |
| 70% B | 15% maleate, 15% acetonate | 30.8 |
| 60% A | 20% azelate, 20% glutamate | 30.2 |
| 48% C, 12% E | 40% glycine | 30.2 |
| 80% D | 15% lactate, 5% serine | 30.0 |
| 100% D (as control) | — | 26.0 |
| Water (as control) | — | 26.4 |
| Difference required for significance of 95% | | 2.7 |
| | Second Series | |
| 70% F | 20% adipate, 10% aspartate | 33.8 |
| 54% C, 26% A | 20% aspartate | 32.8 |
| 70% D | 25% aspartate, 5% malate | 31.9 |
| 60% F | 20% tartarate, 20% glutamate | 31.7 |
| 80% B | 10% aspartate, 10% itaconate | 31.2 |
| 70% D | 15% malate, 15% leucine | 30.7 |
| 70% D | 25% valine, 5% sebacate | 30.7 |
| 60% F | 25% acetonate, 15% succinate | 30.1 |
| 20% C, 40% A | 20% glutarate, 20% glycine | 30.0 |
| 64% C, 16% E | 15% citrate, 5% serine | 29.9 |
| 70% B | 25% tartarate, 5% sebacate | 29.8 |
| 70% A | 30% itaconate | 29.4 |
| 60% F | 25% malate, 15% citrate | 29.4 |
| 56% C, 14% E | 30% aspartate | 28.7 |
| 80% A | 10% lactate, 10% fumarate | 27.6 |
| 15% C, 45% A | 20% fumarate, 20% alunine | 27.6 |
| 54% C, 26% A | 20% valine | 27.3 |
| 54% C, 26% A | 20% leucine | 26.9 |
| 80% B | 15% lactate, 5% glycollate | 26.8 |
| 20% C, 60% E | 10% alanine, 10% serine | 26.3 |
| 100% D (as control) | — | 21.5 |
| Water (as control) | — | 20.9 |
| Difference required for significance at 95% | | 3.1 |

EXAMPLE V

Example IV was repeated using the ammonium and ethanolamine salts of some of the acids proposed.

| | Water binding capacity |
|---|---|
| 30C/30A/40 triethanolamine adipate | 33.20 |
| 40C/10A/10 diethanolamine malate/10 glycine | 30.96 |
| 80A/10 sodium adipate/10 ammonium aspartate | 30.53 |
| 80/20A (control) | 26.35 |
| Water (control) | 25.55 |
| Difference for significance (p = 0.05) | 2.44 |

All moisturizer formulations are significantly better than both the controls.

EXAMPLE VI

A series of test bars were prepared using the actives and moisturising components (as the sodium salts) set out in the following table. The bars had satisfactory properties and the moisturising property is demonstrated by the results. The water binding capacities were measured using the test described previously in Example III.

| Mixture A is | Sodium coconut isothionate | 54% |
|---|---|---|
| | Stearic acid | 25% |
| | Sodium tallow soap | 9% |
| | Sodium isothionate | 7% |
| | Sodium dodecyl-benzene sulphonate | 3% |
| Mixture B is | Sodium coconut isothionate | 78% |
| | $C_{10}$–$C_{18}$ fatty acids | 22% |

MSG is monosodium glutamate; in the bar as formed the glutamate may be present as the disalt and/or free acid.

TABLE 1

| Formulation | | Water binding capacity |
|---|---|---|
| 60% A | 40% Adipate | 26.6 |
| 60% A | 27% Adipate 13% MSG | 22.4 |
| 60% A | 13% Adipate 27% MSG | 24.4 |
| 60% B | 40% Adipate | 25.2 |
| 60% B | 27% Adipate 13% MSG | 24.8 |
| 45% B 15% Soap | 27% Adipate 13% MSG | 24.1 |
| 60% A | 40% Malate | 23.4 |
| 60% A | 27% Malate 13% MSG | 22.8 |
| 60% A | 13% Malate 27% MSG | 25.1 |
| 60% B | 40% Malate | 24.4 |
| 45% B 15% Soap | 40% Malate | 24.3 |
| 45% B 15% Soap | 27% Malate 13% MSG | 23.1 |
| 100% A (control) | | 17.4 |
| 45% B 15% Soap | 40% Adipate | 25.1 |
| 45% B 15% Soap | 13% Adipate 27% Lactate | 24.4 |
| 45% B 15% Soap | 27% Adipate 13% Lactate | 27.0 |
| 45% B 15% Soap | 27% Adipate 13% MSG | 26.0 |
| 45% B 15% Soap | 40% Malate | 25.2 |
| 45% B 15% Soap | 27% Malate 13% Lactate | 25.5 |
| 45% B 15% Soap | 13% Malate 27% Lactate | 20.1 |
| 100% A (control) | | 18.0 |

These bars of the invention were found to have good moisturising properties in handwashing and good physical properties in processing and in-use.

It will be noted that in some bars the adipate or malate has been replaced with lactate or glutamate but the total of additives is at least 20% by weight.

EXAMPLE VII

Series of bars containing 20%, 25%, 30%, 35%, 40%, 45%, 50% and 55% of adipate or malate or 50:50 mixtures thereof were made. They were found to have good moisturizing and physical properties.

EXAMPLE VIII

The skin treatment composition also may be made in accordance with the conventional technology. Thus a typical cream or lotion may comprise water, an oily or waxy substance, an emulsifier, a perfume, a preservative and a colouring agent, together with one or more of the moisturizers of Example I. A viscosity modifier may also be included if necessary.

The above ingredients may be selected from those usual in the cosmetic art, for example: the oily or waxy substance may be a wax ester, a steroid alcohol, a fatty alcohol, a triglyceride ester, a phospholipid, a polyhydric alcohol ester, a fatty alcohol ester, an alkyl fatty ester, a hydrocarbon, a hydrophilic beeswax derivative or a silicone oil.

The nature of the vehicle employed is not an essential part of the invention.

Formulations usable with the materials of the invention are given in "Modern Cosmeticology" volumes I and II of Ralph G Harry published by Leonard Hill (Books) Limited in 1962 and 1963.

The materials of the invention can be incorporated by the known methods into the lotions, creams and other topical application liquids or pastes.

The amount employed will be above about 1% by weight, preferably above about 5% by weight and more preferably above 10% and 20% by weight. The upper limit will be about 50% by weight, preferably less than 40% by weight.

What is claimed is:

1. A detergent bar for increasing the water retention properties of skin containing (a) from about 20% to about 55% by weight of a moisturizing component selected from the group consisting of:

(i) dicarboxylic acids of the formula:

$$COOH-R-COOH$$

and the water soluble salts thereof, wherein R is a hydrocarbon chain containing from 2 to 8 carbon atoms and is branched or unbranched, and saturated or unsaturated;

(ii) the hydroxy acids tartaric acid, citric acid, acetonic acid, glycollic acid and malic acid and the water soluble salts thereof;

(iii) amino acids of the formula:

$$R_3R_4C(NH_2)COOH$$

in which $R_3$ and $R_4$ are each hydrogen, alkyl, hydroxyalkyl, $-CH_2COOH$, amino-alkyl, or the water soluble salts thereof, the alkyl in each of said groups having 1 to 4 carbon atoms; and wherein the hydrocarbon chain is branched or unbranched, and saturated or unsaturated; and (iv) mixtures of the compounds defined in paragraphs i, ii or iii, and (b) from about 45% to about 80% by weight of an anionic, cationic, nonionic or amphoteric detergent active material for use in said detergent bar.

2. The detergent bar defined in claim 1 wherein the hydroxyalkyl group set forth in the definition of $R_3$ or $R_4$ for the amino acid formula, is a monohydroxyalkyl.

3. The detergent bar defined in claim 1 wherein the moisturizing component is selected from the group of dicarboxylic acids comprising succinic acid, glutaric acid, adipic acid, azelaic acid, sebacic acid, fumaric acid, itaconic acid, and the water soluble salts thereof.

4. The detergent bar defined in claim 1 wherein the moisturizing component is selected from the group consisting of glycine, alanine, valine, leucine, isoleucine, threonine, serine, aspartic acid and the water soluble salts thereof.